(12) United States Patent
Leigh et al.

(10) Patent No.: US 10,076,263 B2
(45) Date of Patent: Sep. 18, 2018

(54) SYSTEM AND METHOD FOR BLOOD BRAIN PERMEABILITY IMAGING (BBPI) USING DYNAMIC SUSCEPTIBILITY CONTRAST MAGNETIC RESONANCE IMAGING

(71) Applicant: The Johns Hopkins University, Baltimore, MD (US)

(72) Inventors: Richard Leigh, Towson, MD (US); Peter B. Barker, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 1094 days.

(21) Appl. No.: 14/015,587

(22) Filed: Aug. 30, 2013

(65) Prior Publication Data

US 2015/0065865 A1 Mar. 5, 2015

(51) Int. Cl.
*A61B 5/055* (2006.01)
*G01R 33/563* (2006.01)
*A61B 5/00* (2006.01)
*G01R 33/56* (2006.01)

(52) U.S. Cl.
CPC ........ *A61B 5/055* (2013.01); *G01R 33/56366* (2013.01); *A61B 5/7285* (2013.01); *G01R 33/5601* (2013.01)

(58) Field of Classification Search
CPC A61B 5/055; A61B 5/7285; G01R 33/56366; G01R 33/5601
See application file for complete search history.

(56) References Cited

U.S. PATENT DOCUMENTS 7,069,068 B1 * 6/2006 Ostergaard ............. A61B 6/507
324/307
2011/0257519 A1 * 10/2011 Bj?rnerud ............. A61B 5/055
600/431

OTHER PUBLICATIONS

Zaharchuk, "Theoretical basis of hemodynamic MR imaging techniques to measure cerebral blood volume, cerebral blood flow, and permeability" 2007 AJNR Am J Neuroradiol 28:1850-1858.
Boxerman JL, et al., "Relative cerebral blood volume maps corrected for contrast agent extravasation significantly correlate with glioma tumor grade, whereas uncorrected maps do not." 2006 AJNR Am J Neuroradiol 27: 859-867.

* cited by examiner

*Primary Examiner* — Peter Luong
(74) *Attorney, Agent, or Firm* — MH2 Technology Law Group LLP (57) ABSTRACT

A system and method for generating dynamic susceptibility contrast information from medical imaging data acquired using a magnetic resonance imaging (MRI) system and from a subject having received a dose of a contrast agent. A plurality of images are acquired of the subject. Using the images, an arrival time correction (ATC) is determined that includes a value for at least one of a time shift variable, a time stretch variable, and an amplitude scale variable. The ATC is applied to a model of dynamic susceptibility contrast that relates a measure of signal change over time with a correction term to dynamic susceptibility contrast information to create a corrected model of dynamic susceptibility contrast including the ATC. At least one contrast agent concentration curve is generated from the plurality of images using the corrected model.

18 Claims, 5 Drawing Sheets

SYSTEM AND METHOD FOR BLOOD BRAIN PERMEABILITY IMAGING (BBPI) USING DYNAMIC SUSCEPTIBILITY CONTRAST MAGNETIC RESONANCE IMAGING

CROSS REFERENCE

N/A

BACKGROUND OF THE INVENTION

The present invention relates to medical imaging. More particularly, the invention relates to magnetic resonance imaging (MRI) systems and methods using an arrival time correction (ATC) for dynamic susceptibility contrast (DSC) based permeability imaging.

When a substance such as human tissue is subjected to a uniform magnetic field (polarizing field $B_0$) applied along, for example, a Z axis of a Cartesian coordinate system, the individual magnetic moments of the spins in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, Mz, may be rotated, or "tipped", into the x-y plane to produce a net transverse magnetic moment $M_t$. A NMR signal is emitted by the excited spins after the excitation signal $B_1$ is terminated, this signal may be received and processed to form an image or produce a spectrum.

The MR signals acquired with an MRI system are signal samples of the subject of the examination in Fourier space, or what is often referred to in the art as "k-space". Typically, a region to be imaged is scanned by a sequence of measurement cycles in which gradients vary according to the particular localization method being used. Each MR measurement cycle, or pulse sequence, typically samples a portion of k-space along a sampling trajectory characteristic of that pulse sequence. This is accomplished by employing magnetic fields ($G_x$, $G_y$, and $G_z$) that have the same direction as the polarizing field $B_0$, but which have a gradient along the respective x, y, and z axes. By controlling the strength of these gradients during each NMR cycle, the spatial distribution of spin excitation can be controlled and the location of the resulting NMR signals can be identified. The acquisition of the NMR signals samples is referred to as sampling k-space, and a scan is completed when enough NMR cycles are performed to adequately sample k-space. The resulting set of received NMR signals are digitized and processed to reconstruct the image using one of many well known reconstruction techniques.

MRI techniques can be used to image the blood-brain barrier (BBB), for example, using dynamic contrast enhanced (DCE), T1-weighted imaging studies. Such methods involve calculation of a measure of permeability, $K^{trans}$. Although DCE MRI has been shown to be a robust research tool, it has yet to become part of standard clinical practice. In part this is due to the time-consuming process of acquiring the images required for generating permeability measures with DCE MRI.

Conversely, dynamic susceptibility contrast (DSC) MRI is a routinely acquired imaging technique most commonly used in ischemic stroke patients or brain tumor patients. In brain tumor patients DSC MRI is used to measure cerebral blood volume (CBV) of the tumor as this has been associated with tumor grade. However, leakage of contrast due to BBB disruption can lead to an underestimation of CBV.

A method for contrast leakage has been described (Zaharchuk G (2007) Theoretical basis of hemodynamic MR imaging techniques to measure cerebral blood volume, cerebral blood flow, and permeability. AJNR Am J Neuroradiol 28: 1850-1858) and applied to brain tumor patients (Boxerman J L, Schmainda K M, Weisskoff R M (2006) Relative cerebral blood volume maps corrected for contrast agent extravasation significantly correlate with glioma tumor grade, whereas uncorrected maps do not. AJNR Am J Neuroradiol 27: 859-867). In order to correct for BBB disruption, a measure of permeability is extracted from the DSC MRI acquisition. This approach generates a measure that has been labeled $K_2$, which is related to $K^{trans}$.

DSC MRI is routinely collected on acute stroke patients at many large academic medical centers as part of the evaluation for treatment. In this setting it is referred to as perfusion weighted imaging (PWI) and provides information about the blood flow to the brain.

Several groups have attempted to extract permeability information from PWI in stroke. However, the approach used in these attempts, which assumes uniform perfusion of the brain, can be subject to error when applied to patients with perfusion deficits, such as acute stroke patients. The delay in contrast delivery to areas of hypoperfusion makes calculation of $K_2$ inaccurate.

Therefore, it would be desirable to have a system and method for extending PWI to all clinical settings patients with perfusion deficits, including those with acute stroke, which often are in particular need of dynamic imaging studies.

SUMMARY OF THE INVENTION

The present invention overcomes the aforementioned drawbacks by providing a system and method for correcting a calculation of a leakage fraction of cerebral blood volume as part of a magnetic resonance imaging (MRI) study of the brain. In particular, a system and method for arrival time correction (ATC) is provided that can be applied prior to a calculation of a leakage of cerebral blood volume.

It is an aspect of the invention to provide a method is disclosed for generating dynamic susceptibility contrast information from medical imaging data acquired using a magnetic resonance imaging (MRI) system and from a subject having received a dose of a contrast agent. The method includes acquiring a plurality of images of the subject and reconstructed from the medical imaging data and determining, using the images, an arrival time correction (ATC) including a value for at least one of a time shift variable, a time stretch variable, and an amplitude scale variable. The method also includes applying the ATC to a model of dynamic susceptibility contrast that relates a measure of signal change over time with a correction term to dynamic susceptibility contrast information to create a corrected model of dynamic susceptibility contrast including the ATC. The method further includes generating at least one contrast agent concentration curve from the plurality of images using the corrected model.

It is another aspect of the invention to provide a magnetic resonance imaging (MRI) system that includes a magnet system configured to generate a polarizing magnetic field about at least a portion of a subject arranged in the MRI system, a magnetic gradient system including a plurality of magnetic gradient coils configured to apply at least one magnetic gradient field to the polarizing magnetic field, and a radio frequency (RF) system configured to apply an RF field to the subject and to receive magnetic resonance signals therefrom. The MRI system also includes a computer system programmed to control the magnetic gradient system and the RF system according to a pulse sequence to acquire medical imaging data including T1 information from the subject. The computer system is also programmed to reconstruct from the medical imaging data a plurality of images and generate, using the images, an arrival time correction (ATC) including a value for at least one of a time shift variable, a time stretch variable, and an amplitude scale variable. The computer system is further programmed to apply the ATC to a model of dynamic susceptibility contrast that relates a measure of signal change over with a correction term to dynamic susceptibility contrast information to create a corrected model of dynamic susceptibility contrast including the ATC. Also, the computer system is programmed to generate at least one contrast agent concentration curve from the plurality of images using the corrected model.

It is yet another aspect of the invention to provide a computer system having a tangible, non-transitory, computer-readable storage medium including instructions that, when executed by the computer system, cause the computer system to access a plurality of images of the subject. The computer system is further caused to determine, using the perfusion images, an arrival time correction (ATC) including a value for at least one of a time shift variable, a time stretch variable, and an amplitude scale variable. The computer system is also caused to apply the ATC to a model of dynamic susceptibility contrast that relates a measure of signal change over time with a correction term to dynamic susceptibility contrast information to create a corrected model of dynamic susceptibility contrast including the ATC. Additionally, the computer system is caused to generate at least one contrast agent concentration curve from the plurality of images using the corrected model.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
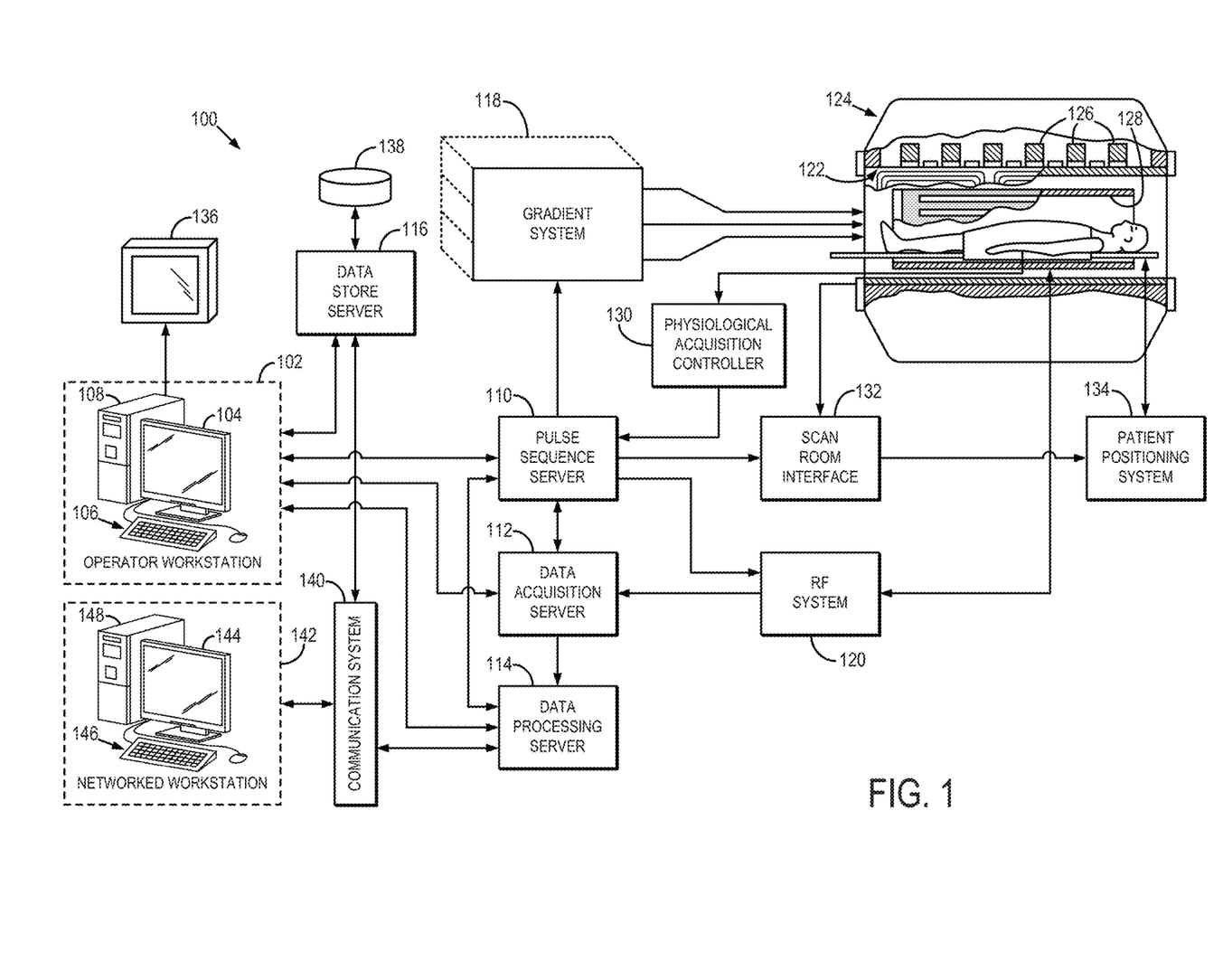
FIG. 1 is a block diagram of an exemplary magnetic resonance imaging ("MRI") system that employs the present invention.

Referring particularly to FIG. 1, an example of a magnetic resonance imaging ("MRI") system 100 is illustrated. The MRI system 100 includes a workstation 102 having a display 104 and a keyboard 106. The workstation 102 includes a processor 108 that is commercially available to run a commercially-available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil, such as a head coil, by the RF system 120 to perform the prescribed magnetic resonance pulse sequence. Responsive MR signals detected by the RF coil 128, or a separate local coil, are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays.

The RF system 120 also includes one or more RF receiver channels. Each RF receiver channel includes an RF preamplifier that amplifies the MR signal received by the coil 128 to which it is connected, and a detector that detects and digitizes the and quadrature components of the received MR signal. The magnitude of the received MR signal may thus be determined at any sampled point by the square root of the sum of the squares of the I and Q components:

$$M = \sqrt{I^2 + Q^2} \qquad (1);$$

and the phase of the received MR signal may also be determined:

$$\varphi = \tan^{-1}\left(\frac{Q}{I}\right). \qquad (2)$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network or communication system 140 to other facilities that may include other networked workstations 142.

The communications system 140 and networked workstation 142 may represent any of the variety of local and remote computer systems that may be included within a given clinical or research facility including the system 100 or other, remote location that can communicate with the system 100. In this regard, the networked workstation 142 may be functionally and capably similar or equivalent to the operator workstation 102, despite being located remotely and communicating over the communication system 140. As such, the networked workstation 142 may have a display 144 and a keyboard 146. The networked workstation 142 includes a processor 148 that is commercially available to run a commercially-available operating system. The networked workstation 142 may be able to provide the operator interface that enables scan prescriptions to be entered into the MRI system 100.

The above-described system can be used to acquire images that indicate the permeability of the blood brain barrier. Specifically, blood brain permeability images are typically generated from standard perfusion weighted imaging (PWI) pulse sequence acquisitions. Such PWI pulse sequences use dynamic susceptibility contrast (DSC) imaging, in which T2* weighted images are acquired in rapid succession with whole brain coverage, usually about one brain every two seconds. However, referring to FIG. 2, a method 200 in accordance with the present invention may utilize an echo-planar imaging (EPI) pulse sequence, such as indicated at process block 202, to acquire baseline data.

Figure 3:
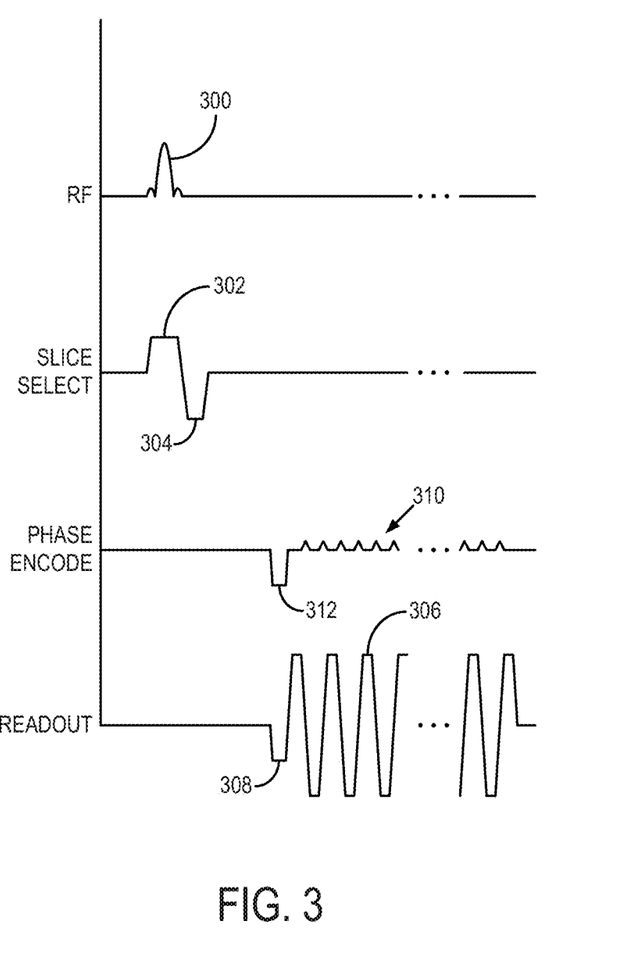
FIG. 3 is a block diagram of an exemplary echo planar imaging ("EPI") pulse sequence for directing the MRI system of FIG. 1 in accordance with the present invention.

An exemplary pulse sequence employed to direct the MRI system to acquire image data is illustrated in FIG. 3. Such an exemplary pulse sequence is a gradient-recalled echo planar imaging ("GE-EPI") pulse sequence. The pulse sequence includes a spatially selective radio frequency ("RF") excitation pulse 200 that is played out in the presence of a slice-selective gradient 302 in order to produce transverse magnetization in a plurality of prescribed imaging slices. The RF excitation pulse is the summation of RF excitation pulses that would be used to separately excite the desired plurality of slice locations and is applied with a flip angle. The slice-selective gradient 302 includes a rephasing lobe 304 that acts to rephase unwanted phase dispersions introduced by the slice-selective gradient 302 such that signal losses resultant from these phase dispersions are mitigated.

Following excitation of the nuclear spins in the prescribed imaging slices, image data is acquired by sampling a series of gradient-recalled echo signals in the presence of an alternating readout gradient 306. The alternating readout gradient may be preceded by the application of a prewinding gradient 308 that acts to move the first sampling point along the frequency-encoding, or readout, direction by a distance $\Delta k_x$ in k-space. Spatial encoding of the echo signals along a phase-encoding direction may be performed by a series of phase encoding gradient "blips" 310, which are each played out in between the successive signals readouts such that each echo signal is separately phase encoded. The phase encoding gradient blips 310 are preceded by the application of a pre-winding gradient 312 that acts to move the first sampling point along the phase-encoding direction a distance $\Delta k_y$ in k-space. Together, the pre-winding gradients 308 and 312 serve to begin the sampling of k-space at a defined k-space location $(k_x, k_y)$.

As is known in the art, the foregoing pulse sequence is repeated a plurality of times with a different slice-selective gradient 302 being applied in each repetition such that multiple sets of a plurality of slice locations are sampled and, as will be described, may be coordinated with administration of a contrast agent, such as gadopentetate dimeglumine (Magnevist; Bayer HealthCare Pharmaceuticals). Gadopentetate dimeglumine is a non-limiting example of but one contrast agent. There are a variety of contrast agents, including contrast agents that are not yet commercially available in particular markets. Each contrast agent has or will have new/different properties when injected. As will be described, the present invention can be used to correct for variations in an arrival time to removed the time delivery and reveal other properties of the agents. Leakage of the BBB, is just being one non-limiting example of an application for the present invention.

The resulting, perfusion data sets can then be reconstructed into T2*-weighted images. More particularly, $K_2$ images can be generated from DSC images. Specifically, referring again to FIG. 2, after a baseline is established, usually 4-5 brain volumes, a weight-based dose of gadolinium (gad) is administered, for example, with a power injector through an intravenous (IV) injection, such as indicated at process block 204. Notably, imaging may continue during the administration of the contrast agent.

Figure 2:
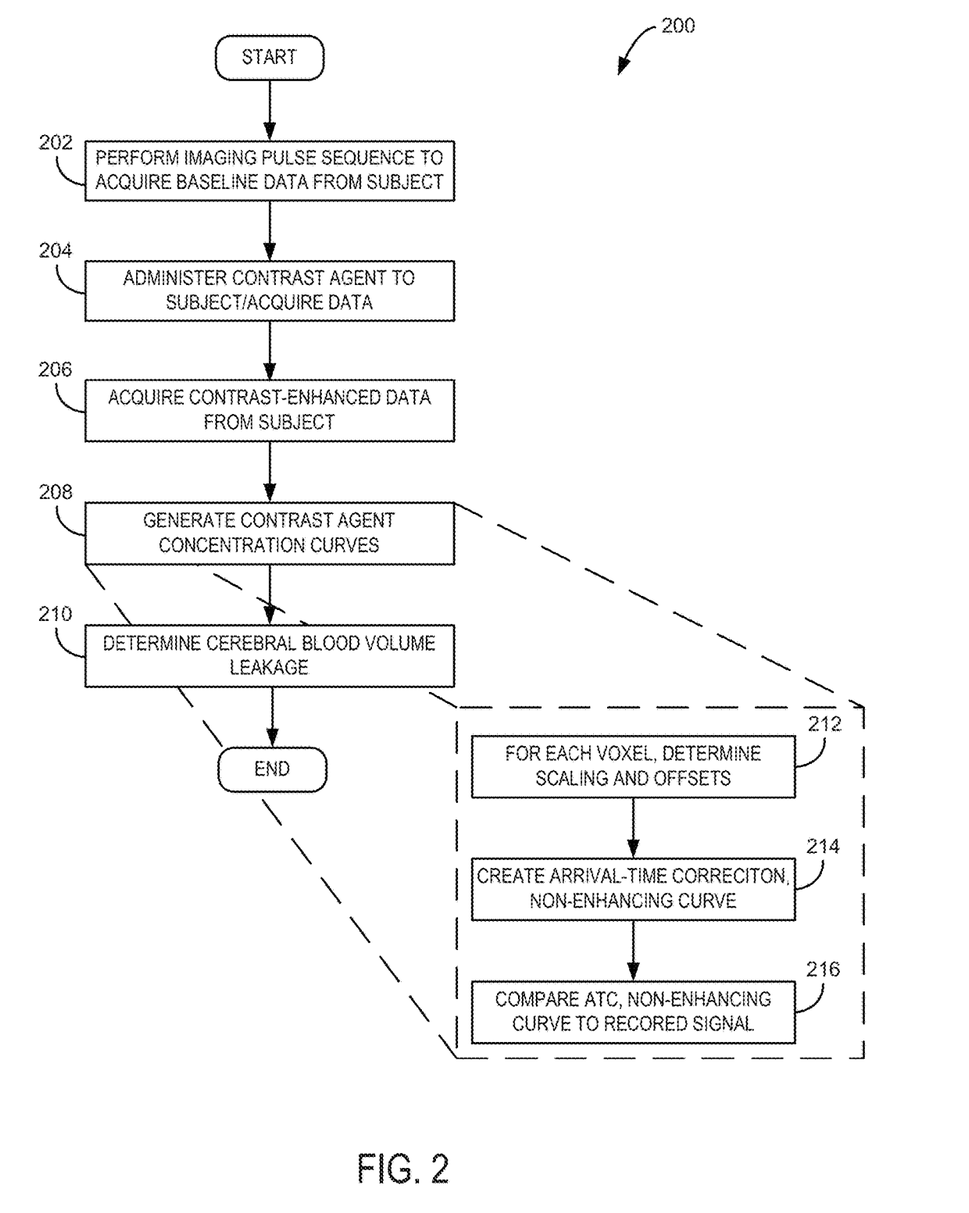
FIG. 2 is a flow chart setting forth the steps of a method in accordance with the present invention and for use with an MRI system such as illustrated in FIG. 1.

At process block 206, contrast-enhanced data is acquired from the subject. As the gadolinium enters the brain, it causes the recorded signal to go down, and then as the gadolinium washes out, the signal comes back up and will eventually approach that of the baseline data acquired from the subject in process block 202, as the gadolinium is excreted by the kidneys. The resulting signal change over time, which is recorded at every voxel, is then converted into a gadolinium concentration curve at process block 208. As will be described, at process block 210, this allows the determination of the fraction of the CBV calculated using the corrected concentration curve.

Although the acquired contrast-enhanced data is T2* weighted, because the data was acquired, for example, using an EPI pulse sequence, the data also has some T1 weighting. The gadolinium causes a decrement in the recorded signal due to the T2* effect; however, the T1 effect increases the recorded signal. Usually the contribution of the T1 effect is negligible because it is proportional to the concentration of gad in the brain tissue, which is essentially zero if the BBB is intact. However, when contrast leaks through the BBB and accumulates in the brain parenchyma, it causes the signal to change due to T1 effects. For instance, it will make the gadolinium concentration curve approach zero faster and even go below baseline in some cases. The present invention recognizes that this phenomenon can be used to create accurate blood brain permeability images (BBPI), because by modeling it, a measure of BBB permeability can be generated that is proportional to this T1 effect. As will be described, BBPIs can generated from the source images of a PWI DSC acquisition.

There are several approaches to using DSC MRI to assess the permeability of the BBB. However, these techniques can suffer from errors, such as described above. A method, such as described by Boxerman et al. (Boxerman J L, Schmainda K M, Weisskoff R M (2006) Relative cerebral blood volume maps corrected for contrast agent extravasation significantly correlate with glioma tumor grade, whereas uncorrected maps do not. AJNR Am J Neuroradiol 27: 859-867) can be used for uncorrected DSC MRI permeability imaging. That is, Boxerman and colleagues modeled the recorded signal as having two components. A first component was due to the T2* effect and a second component was due to the T1 effect. To accurately use this model, there must be an area of intact tissue. For stroke patients, the unaffected hemisphere can be used. The model assumes that the recorded concentration curve can be represented by a linear combination of a scaled concentration curve from intact tissue minus a correction term, in this example, a leakage term. The leakage term is a fraction of the cerebral blood volume. This fraction, referred to as K2, is a relative measure of the amount of BBB damage. Thus, BBPIs using this model are essentially K2 images. However, there is an inaccurate assumption in the Boxerman model. The Boxerman model assumes that the temporal delivery of contrast is equal throughout the brain. However, in reality, this is not the case since the temporal delivery of contrast to different parts of the brain is related to a variety of factors including vascular distance from the heart. In stroke patients, this variablity is particularly prominent since vascular obstructions can cause unpredictable changes in blood flow patterns which affect the temporal delivery of contrast. Perfusion deficits result in a delay in contrast delivery, hence the prolonged TTPs In particular, changes in tissue contrast agent concentration can be measured as changes in relaxivity as follows:

$$\Delta R2*(t) = \left(\frac{-1}{TE}\right)\ln\left(\frac{S(t)}{S_0}\right); \quad \text{Eqn. (3)}$$

where TE is the time to echo, S(t) is the signal intensity in the voxel at time t, and $S_0$ is the baseline signal intensity prior to delivery of the contrast bolus. When contrast leaks through the BBB into the parenchyma, the measured signal is more accurately characterized by adding a term to equation (3) to account for T1 effects as follows:

$$\Delta R2*(t)_{measured} = \Delta R2*(t) - \frac{TRe^{\left(-\frac{TR}{T1}\right)}}{TE\left(1-e^{\left(-\frac{TR}{T1}\right)}\right)}R_1 C_{tissue}(t); \quad \text{Eqn. (4)}$$

where TR is the time to repetition, $R_1$ is 1/T1, and $C_{tissue}(t)$ is the concentration of contrast in the tissue at time t. The amount of contrast leakage for each voxel is estimated by assuming that the measured relaxivity change is a linear combination of the average signal in non-enhancing voxels and some fraction of its time integral as follows:

$$\Delta \tilde{R}2*(t) = K_1 \overline{\Delta R2*(t)} - K_2 \int_0^t \overline{\Delta R2*(t')}dt'; \quad \text{Eqn. (5)}$$

where $\Delta \tilde{R}2*(t)$ is the measured, uncorrected change in relaxivity, $\overline{\Delta R2*(t)}$ is the average signal for a region of nonenhancing voxels, and $$\int_0^t \overline{\Delta R2*(t')}dt'$$

is the integral of the average signal for a region of non-enhancing voxels, which is essentially the average cerebral blood volume (CBV). The term $K_1\overline{\Delta R2*(t)}$ represents the uncontaminated portion of the measured signal as the average signal of non-enhancing values times a scaling factor $K_1$. The $$K_2 \int_0^t \overline{\Delta R2*(l)}dl$$

term reflects the effect due to leakage and is represented as the average CBV of non-enhancing tissue times $K_2$, where $K_2$ is a fraction between 0 and 1. Thus, when equation 5 is solved for $K_2$, the fraction of the average CBV that has leaked at each voxel is approximated.

Using T1-weighted, post-contrast images as a guide, regions of interest (ROIs) can be outlined in the ischemic hemisphere to delineate BBB disruption on the DSC source images. This can be done visually or by automated algorithm using the T1-weighted, post-contrast images as compared against the T2* baseline DSC source images. The ROI may then be flipped into the contralateral hemisphere to create a control ROI.

Inherent in the MRI DSC permeability imaging technique described above is the assumption that the recorded signal for a given voxel can be represented as a scaled version of the average signal. For example, if a voxel had no contrast leakage, $K_2$ would be zero and equation 5 would become:

$$\Delta \tilde{R}2*(t) = K_1 \overline{\Delta R2*(t)} \qquad \text{Eqn. (6).}$$

However, this assumption fails when there is a delay in contrast delivery such as in a perfusion deficit of a stroke patient. The shape of the measured curve is often very different in hypoperfused tissues. As the curve becomes broader, it peaks later and has a different area underneath it.

In accordance with the present invention, an arrival time correction (ATC) is provided by adjusting $\overline{\Delta R2*(t)}$ on a voxel-by-voxel basis to fit the true morphology of the recorded signal. Specifically, a term can be defined:

$$\overline{\Delta R2*(t)}_{ATC} = \gamma \overline{\Delta R2*}\left(\frac{t+\tau}{\alpha}\right); \qquad \text{Eqn. (7)}$$

where $\overline{\Delta R2*(t)}_{ATC}$ is the average signal after ATC, $\gamma$ is a magnitude scaling factor, $\alpha$ is a time scaling factor, and $\tau$ is a time offset. Thus, equation 5 becomes:

$$\Delta \tilde{R}*(t) = \overline{\Delta R2*(t)}_{ATC} - K_2 \int_0^t \overline{\Delta R2*(t')}_{ATC} dt'; \qquad \text{Eqn. (8)}$$

where $K_1$ is dropped because scaling has been performed as part of the ATC. Using a multiple least-squares approach, the values for $\gamma$, $\alpha$, and $\tau$ are determined by minimizing the following over a range of values:

$$\min \sqrt{(\overline{\Delta R2*(t)}_{ATC})^2 - (\Delta \tilde{R}2*(t))^2} \qquad \text{Eqn. (9).}$$

Thus, at every voxel $\gamma$, $\alpha$, and $\tau$ are determined to create an ATC, non-enhancing curve to compare with the recorded signal to determine if there is evidence of BBB disruption. That is, referring again to FIG. 2, to generate the contrast agent concentration curves at process block 208, some sub steps may occur. Specifically, at process block 212 any scaling factors and offsets, such as $\gamma$, $\alpha$, and $\tau$, are determined for each voxel. At process block 214, this analysis is used to create an ATC, non-enhancing curve that, at process block 216, is compared with the recorded signal to determine if there is evidence of BBB disruption. The $K_2$ value generated again represents the fraction of the CBV that has leaked. However, in this case, the $K_2$ value is the fraction of the CBV calculated using the corrected concentration curve, such as indicated at process block 210.

Figure 4A:
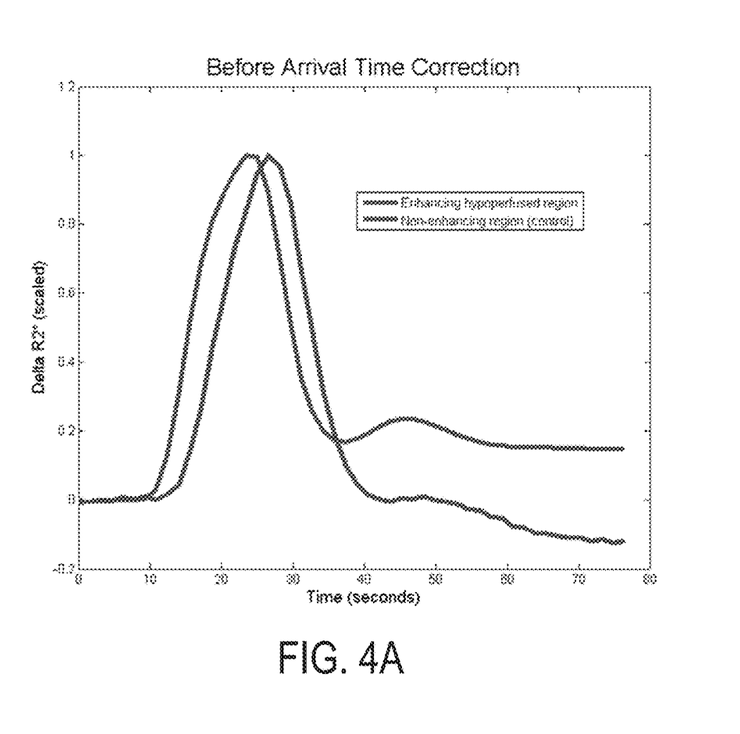
FIGS. 4A and 4B are graphs showing the delta R2* for non-enhancing (control) and enhancing hypoperfused regions before and after arrival time correction (ATC), respectively.
Figure 4B:
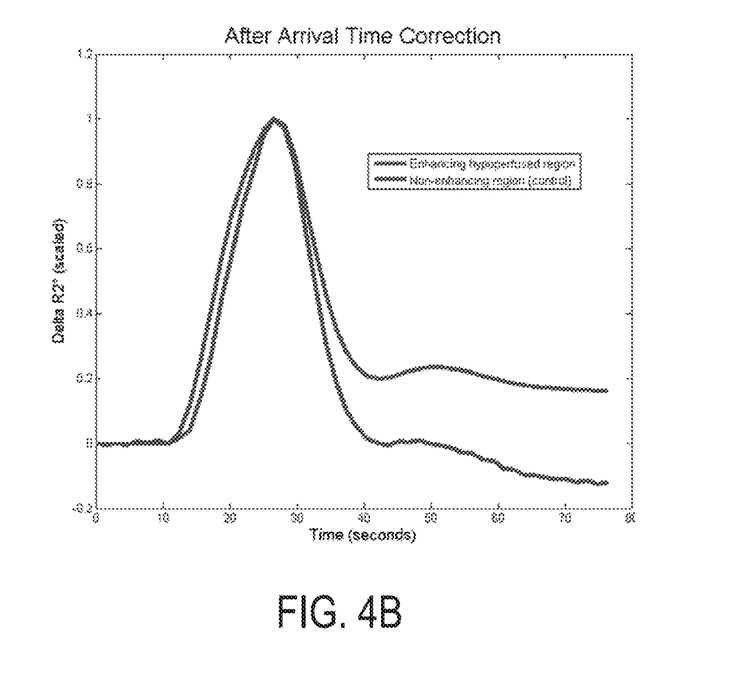

An example of how the non-enhancing curve is adjusted with the ATC is shown in FIGS. 4A and 4B. In FIG. 4A, due to even a small delay in time-to-peak, the control signal appears to approach baseline faster, thus, obscuring the phenomenon being measured. However, as shown in FIG. 4B, after the ATC has been applied to the control, it becomes evident that the enhancing region signal is approaching the baseline faster due to the T1 effect of contrast accumulation in the parenchyma.

Thus, in order to utilize a model such as described above, the gadolinium concentration curves must be corrected for any time delays. The present invention provides an arrival time correction (ATC) to achieve this end. The ATC is performed by introducing new variables, such as a time shift, a time stretch, and an amplitude scale. These variables can be determined on a voxel-by-voxel basis to remove the effects of any perfusion deficits. They also capture unique measures of the perfusion deficits which may have other applications in stroke treatment. The ATC can be used to compensate for blood flow changes in stroke patients; however, can also be used to improve the performance of such techniques in all patients because blood flow in the brain is heterogeneous even in normal brains.

Receiver Operating Characteristic (ROC) Analysis

Voxels in the ROI of the ischemic hemisphere can be designated as having BBB disruption, while voxels from the control ROI can be designated as no BBB disruption. $K_2$ values can be calculated in the permeability analysis as a fraction of the CBV, thus, they range from 0 to 1. Using the $K_2$ values from the permeability analysis, voxels can be divided into 2 groups based on a threshold, for example, a threshold varied from 0 to 1. For instance, a threshold of 0.2 may indicate that 20 percent of the CBV, as represented by T1 signal change, would have to be measured as leakage on the $K_2$ image in order for it to be considered as representative of true BBB disruption.

For every given threshold the classification of voxels as having BBB damage or not will result in true positives, false positives, true negatives, and false negatives. Thus, for every threshold, a sensitivity and specificity can be generated for both the corrected and uncorrected permeability images. Plotting sensitivity versus 1-specificity results in an ROC curve. A perfect test results in a curve that intersects the top left hand corner. This indicates that a threshold was identified that has a sensitivity of 1 and a specificity of 1. The ROC curve for a random guess results in a diagonal line from bottom left to top right. The area under the curve (AUC) is a measure of the overall performance of the test. For a perfect test, the AUC would be 1, while the AUC for a random guess curve would be 0.5. ROC curves can be generated to compare the performance of the corrected versus uncorrected images at identifying BBB damage.

For example, in one study, nine patients and 13 MRI scans were selected as meeting the inclusion criteria and were included in the analysis. The mean age of the patients was 60 years old, and 6 of the patients were female. The time from stroke to MRI scan ranged from 2 hours and 44 minutes to 10 days, 7 hours and 41 minutes. The median time from stroke to MRI was 2 days, 1 hour and 52 minutes. Four of the 9 patients had a witnessed time of stroke onset. For the remaining patients the "last known normal" time was used. Four patients had left hemisphere anterior circulation strokes, and 5 patients had right hemisphere anterior circulation strokes.

Figure 5:
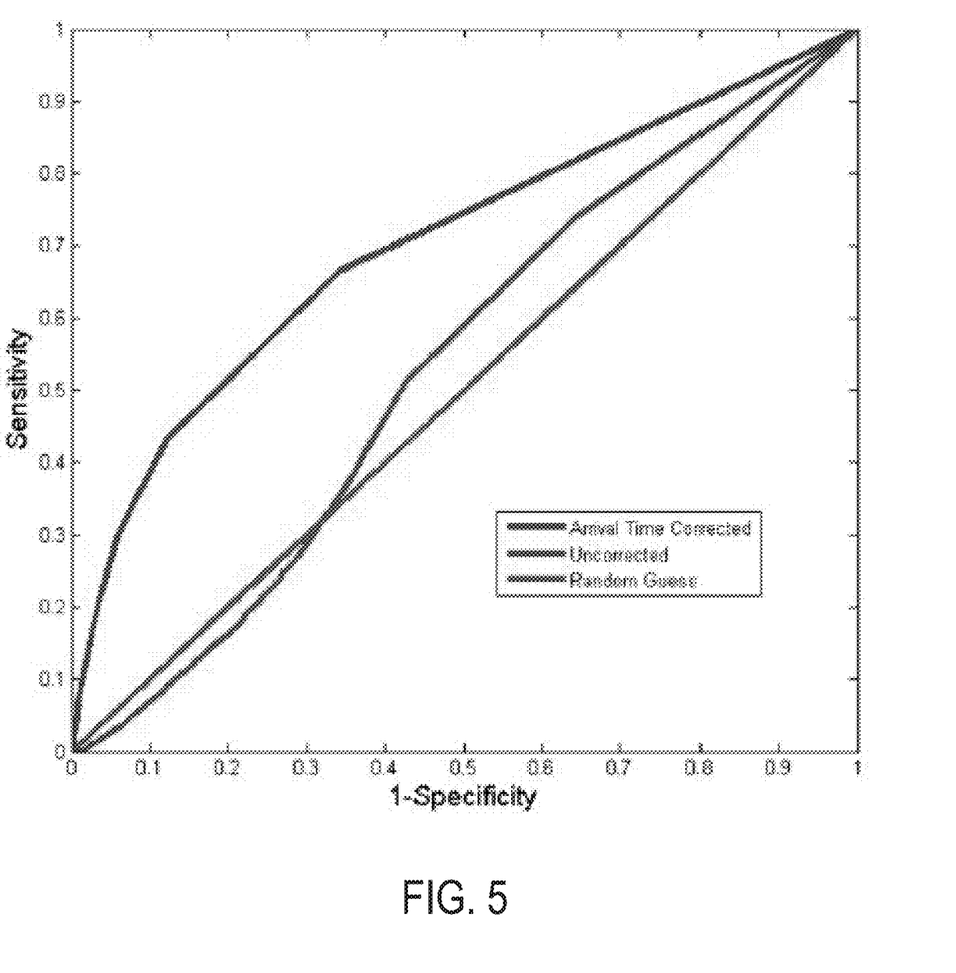
FIG. 5 is a graph showing receiver-operator characteristic (ROC) curves, which demonstrate the ability to correctly identify enhancing tissue, are plotted before and after arrival time correction (ATC).

The ROC curves were plotted for the uncorrected and the ATC techniques and are provided in FIG. 5. The AUC for the uncorrected method was 0.53. ATC improved the ability to detect BBB disruption to an AUC of 0.70. Thresholds of 0.005 (0.5% of CBV) for the uncorrected and 0.011 (1.1% of CBV) for the corrected were identified as the best (i.e. resulted in a sensitivity/specificity point closest to the top-left hand corner of the ROC curve). The sensitivity improved from 0.51 to 0.67 and the specificity improved from 0.57 to 0.66. Visual inspection of the ROC curve reveals that the performance of the uncorrected analysis was worse than random guess at some thresholds.

It has been shown that the arrival time correction (ATC) improves the ability of perfusion-weighted imaging to detect breakdown of blood-brain barrier following stroke. The role of BBB disruption in stroke patients has been investigated by a variety of measurement techniques. However, the present invention and studies based thereon shows that damage to the BBB in acute stroke patients may predict response to treatment. More specifically, damage to the BBB may provide a measure of the risk of intracranial hemorrhage (ICH), which is the most serious complication of thrombolytic stroke treatment. T1, post-contrast imaging is the most commonly used clinical method for detecting damage to the BBB. It has been shown to be very specific for predicting ICH in stroke patients but not very sensitive. FLAIR-based, post-contrast imaging, referred to as hyperintense acute reperfusion marker (HARM), has also been investigated and has been shown to predict hemorrhagic transformation and poor outcome in stroke patients. However, this approach requires a delay between the administration of contrast and image acquisition on the order of hours and thus is not practical for management of acute stroke, which takes place on the order of minutes. The use of DSC MRI to detect BBB has also been investigated using various approaches, but none of these approaches uses an ATC prior to calculating permeability. Despite this body of literature, permeability imaging has not found its way into clinical use.

Using the present invention, it has been demonstrated that, in stroke patients with evidence of BBB disruption, ATC of DSC MRI improves identification of permeability derangements. Specifically, based on the ROC analysis of this study, ATC improves the performance of DSC MRI based permeability imaging, such as by T1, post-contrast imaging. The ROC analysis also reveals that, in the absence of ATC, DSC MR based permeability imaging can be worse than random guess at identifying damage to the BBB.

Since perfusion deficits, when not corrected for, can be erroneously identified as permeability derangements due to assumptions of the model, the present invention can substantially improve clinical information. Specifically, traditional models assume that the shape of the curve of the recorded signal will be the same throughout the brain, even in hypoperfused tissue. In reality, the recorded curve in hypoperfused tissue has a different morphology. Thus, the present invention has been validated to show that ATC of the recorded curve adjusts its morphology and improves the performance of such models. To this end, the present invention can likewise be used for clinical applications, such as hemorrhagic stroke, brain tumors, vascular dementia, and multiple sclerosis.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for generating dynamic susceptibility contrast information from medical imaging data acquired using a magnetic resonance imaging (MRI) system and from a subject having received a dose of a contrast agent, the method comprising:
controlling the MRI system to acquire a plurality of images of the subject and reconstructed from the medical imaging data from the MRI system;
determining, using the plurality of images, an arrival time correction (ATC) for the contrast agent from a time of dose delivery to a later subsequent time, wherein the ATC includes a value for at least one of a time shift variable, a time stretch variable, and an amplitude scale variable for each voxel in a region-of-interest of one or more of the plurality of images, wherein the ATC corrects for variations in temporal delivery of the contrast agent to a damaged region and to an undamaged region of a brain of the subject;
applying the ATC to a model of dynamic susceptibility contrast that relates a measure of signal change over time with a correction term to dynamic susceptibility contrast information;
creating a corrected model of dynamic susceptibility contrast including the ATC;
generating at least one contrast agent concentration curve from the plurality of images using the corrected model; and
diagnosing evidence of blood-brain barrier (BBB) disruption by comparing the at least one contrast agent concentration curve with a non-enhanced curve.

2. The method of claim 1 wherein the diagnosing comprises quantifying a disruption of the (BBB) of the subject.

3. The method of claim 1 wherein the determining the ATC comprises determining a value for each of the time shift variable, the time stretch variable, and the amplitude scale variable, wherein the ATC includes a value for each of the time shift variable, the time stretch variable, and the amplitude scale variable.

4. The method of claim 1 wherein the images include a T2* weighting.

5. The method of claim 1 wherein the value for at least one of the time shift variable, the time stretch variable, and the amplitude scale variable are derived using imaging information.

6. The method of claim 1 further comprising using the at least one contrast agent concentration curve to analyze a stroke suffered by the subject.

7. The method of claim 1 further comprising using the at least one contrast agent concentration curve to analyze heterogeneous blood flow through a brain of the subject.

8. The method of claim 1, wherein the ATC is given by $$\gamma \overline{\Delta R2^*}\left(\frac{t+\tau}{\alpha}\right)$$

where $\gamma$ is the amplitude scale variable, $\alpha$ is the time stretch variable, $\tau$ is the time shift variable, R is a relaxivity that is a measure of tissue contrast agent concentration, and t is time.

9. A magnetic resonance imaging (MRI) system, comprising:
a magnet system configured to generate a polarizing magnetic field about at least a portion of a subject arranged in the MRI system;
a magnetic gradient system including a plurality of magnetic gradient coils configured to apply at least one magnetic gradient field to the polarizing magnetic field;
a radio frequency (RF) system configured to apply an RF field to the subject and to receive magnetic resonance signals therefrom;
a computer system programmed to:
control the magnetic gradient system and the RF system according to a pulse sequence to acquire medical imaging data including T1 information from the subject;

reconstruct from the medical imaging data a plurality of images;

generate, using the images, an arrival time correction (ATC) for the contrast agent from a time of dose delivery to a later subsequent time, wherein the ATC includes a value for at least one of a time shift variable, a time stretch variable, and an amplitude scale variable for each voxel in a region-of-interest of one or more of the plurality of images, wherein the ATC corrects for variations in temporal delivery of the contrast agent to a damaged region and to an undamaged region of a brain of the subject;

apply the ATC to a model of dynamic susceptibility contrast that relates a measure of signal change over time with a correction term to dynamic susceptibility contrast information;

creating a corrected model of dynamic susceptibility contrast including the ATC;

generate at least one contrast agent concentration curve from the plurality of images using the corrected model; and diagnosing evidence of blood-brain barrier (BBB) disruption by comparing the at least one contrast agent concentration curve with a non-enhanced curve.

10. The system of claim 9 wherein the pulse sequence includes an echo planar imaging pulse sequence.

11. The system of claim 9 wherein the computer system is further programmed to quantify a disruption of the BBB of the subject using the at least one contrast agent concentration curve.

12. The system of claim 9 wherein the computer system is further programmed to determine a value for each of the time shift variable, the time stretch variable, and the amplitude scale variable.

13. The system of claim 12 wherein the computer is further programmed to generate the ATC to include a value for each of the time shift variable, the time stretch variable, and the amplitude scale variable.

14. The system of claim 9 wherein the images include a T2* weighting.

15. The system of claim 9 wherein the value for at least one of the time shift variable, the time stretch variable, and the amplitude scale variable are derived using the T1 information.

16. The system of claim 9, wherein the ATC is given by $$\gamma \overline{\Delta R2^*}\left(\frac{t+\tau}{\alpha}\right)$$

where $\gamma$ is the amplitude scale variable, $\alpha$ is the time stretch variable, $\tau$ is the time shift variable, R is a relaxivity that is a measure of tissue contrast agent concentration, and t is time.

17. A tangible, non-transitory, computer-readable storage medium including instructions that, when executed by a computer system, cause the computer system to:

control a magnetic resonance imaging (MRI system to access a plurality of perfusion images including T1 information of a subject;

determine, using the plurality of perfusion images, an arrival time correction (ATC) for the contrast agent from a time of dose delivery to a later subsequent time, wherein the ATC includes a value for at least one of a time shift variable, a time stretch variable, and an amplitude scale variable for each voxel in a region-of-interest of one or more of the plurality of images, wherein the ATC corrects for variations in temporal delivery of the contrast agent to a damaged region and to an undamaged region of a brain of the subject;

apply the ATC to a model of dynamic susceptibility contrast that relates a measure of signal change over time with a correction term to dynamic susceptibility contrast information;

create a corrected model of dynamic susceptibility contrast including the ATC;

generate at least one contrast agent concentration curve from the plurality of perfusion images using the corrected model; and diagnosing evidence of blood-brain barrier (BBB) disruption by comparing the at least one contrast agent concentration curve with a non-enhanced curve.

18. The computer system of claim 17, wherein the ATC is given by $$\gamma \overline{\Delta R2^*}\left(\frac{t+\tau}{\alpha}\right)$$

where $\gamma$ is the amplitude scale variable, $\alpha$ is the time stretch variable, $\tau$ is the time shift variable, R is a relaxivity that is a measure of tissue contrast agent concentration, and t is time.

* * * * *